United States Patent [19]

Bauer

[11] Patent Number: 5,026,952
[45] Date of Patent: Jun. 25, 1991

[54] PROCESS FOR SEPARATING $C_2+$ OR $C_3+$ OR $C_4$ HYDROCARBONS FROM A GASEOUS MIXTURE

[75] Inventor: Heinz Bauer, Munich, Fed. Rep. of Germany

[73] Assignee: Linde Aktiengesellschaft, Wiesbaden, Fed. Rep. of Germany

[21] Appl. No.: 328,192

[22] PCT Filed: Aug. 4, 1987

[86] PCT No.: PCT/EP87/00427
§ 371 Date: Feb. 2, 1989
§ 102(e) Date: Feb. 2, 1989

[87] PCT Pub. No.: WO88/00936
PCT Pub. Date: Feb. 11, 1988

[30] Foreign Application Priority Data
Aug. 6, 1986 [DE] Fed. Rep. of Germany ....... 3626560
Aug. 6, 1986 [DE] Fed. Rep. of Germany ....... 3626561

[51] Int. Cl.$^5$ .................................................. C07C 7/00
[52] U.S. Cl. .......................................... 585/800; 55/80; 208/347; 208/350; 208/353; 208/358
[58] Field of Search ............... 585/800; 208/347, 350, 208/353, 358; 55/80

[56] References Cited

U.S. PATENT DOCUMENTS

| | | | |
|---|---|---|---|
| 3,338,825 | 8/1967 | Taggart | 208/350 |
| 3,494,751 | 2/1970 | Streich | 208/350 |
| 4,019,979 | 4/1977 | Nolley, Jr. | 208/353 |
| 4,496,380 | 1/1985 | Harryman | 62/24 |

FOREIGN PATENT DOCUMENTS

| | | | |
|---|---|---|---|
| 0126309 | 11/1984 | European Pat. Off. . | |
| 3445961 | 6/1980 | Fed. Rep. of Germany | 585/800 |
| 2917505 | 11/1980 | Fed. Rep. of Germany | 585/800 |
| 2110808 | 6/1983 | United Kingdom . | |

*Primary Examiner*—Curtis R. Davis
*Attorney, Agent, or Firm*—Millen, White & Zelano

[57] ABSTRACT

The aim is to separate, by cooling and partial condensation of $C_2+$, $C_3+$ or $C_4$ hydrocarbons contained in a gas mixture comprising, in addition to these components, even lighter constituents. For this purpose, the gas mixture is at first cooled until condensation of a smaller part of the hydrocarbons to be separated, after which the mixture is fed into the lower region of a fractionating column. A gaseous fraction is removed from the upper region of said column and is then again cooled and partly condensed in a heat exchanger, after which this partly condensed fraction is conveyed to the top of the fractionating column in the form of a return flow. In the case of $C_4$ separation, the $C_4$ hydrocarbons must represent more than 50% of the hydrocarbons contained in the gas.

25 Claims, 4 Drawing Sheets

PROCESS FOR SEPARATING $C_{2+}$ OR $C_{3+}$ OR $C_4$ HYDROCARBONS FROM A GASEOUS MIXTURE

BACKGROUND OF THE INVENTION

The invention relates to a process for separating $C_{2+}$ or $C_{3+}$ hydrocarbons, or $C_4$ hydrocarbons, from a gaseous mixture containing these components and lighter constituents by cooling and rectification.

Partial condensation represents a simple separating process wherein a gaseous stream to be fractionated is separated into two fractions of differing composition merely by lowering the temperature to below the dew point and by subsequent phase separation in a separator. This procedure constitutes a poorly selective separation with only one equilibrium stage wherein higher-boiling components are enriched in the condensate and lower-boiling constituents are enriched in the gaseous phase. On account of the low separating selectivity, such processes are utilized essentially as preliminary separating stages upstream of a larger fractionating unit, for example upstream of a rectifying column.

A more selective separation, however, at the cost of increased expenditure, is possible, for example, when using a dephlegmator or, respectively, reflux condenser. In a reflux condenser, the upwardly flowing gaseous mixture is cooled by indirect heat exchange with a cooling medium, preferably the cold, uncondensed gas; with increasing cooling action, an increasing number of components of the gaseous mixture is condensed and drops downwards in the opposite direction to the gaseous stream. The downwardly dropping liquid enters into heat exchange and mass transfer with the rising gaseous mixture so that a rectifying gas separation takes place within the reflux condenser. The heavy component to be separated can be withdrawn from the bottom of the reflux condenser whereas the cold gas, freed extensively of the heavy component and exiting at the top from the reflux condenser, can be recycled, for example after a cold-producing expansion, countercurrently to the gaseous mixture to be fractionated, as a coolant to the reflux condenser where it is heated approximately again to the initial temperature by indirect heat exchange before being passed on to further usage. Heat exchangers are ordinarily installed in the reflux condenser for cooling the gaseous mixture; these heat exchangers, on account of their specific design, for example as wound heat exchangers or plate-type heat exchangers, effect an intensive contact between the upwardly flowing gaseous mixture and the downwardly dropping liquid.

EP-A 126,309, for example, discloses such a process wherein a gaseous mixture containing at most 10% $C_4$ hydrocarbons and at least 65% methane and lighter components is fractionated with the use of a dephlegmator or reflux condenser.

The use of a reflux condenser instead of a usual rectifying column offers advantages, in particular, under the viewpoints of thermodynamics since the return flow required for rectification of the gaseous mixture is produced within the reflux condenser proper at a sliding temperature, whereas in case of a rectifying column the entire return flow must be made available at maximally low temperature and must be introduced into the head of the column. The fact that the return flow is formed with sliding temperature from the gaseous mixture proper can, however, also be an obstacle to the use of a reflux condenser in special cases. If, for instance, the gaseous mixture to be fractionated consists essentially of components having widely spaced-apart boiling points, then a large portion of the higher-boiling component condenses already shortly below the dew point in the lower region of the reflux condenser. However, in case this component is to be separated in high yield, temperatures must be set to far below the dew point, for example up to 100° C. below the dew point. Such an irregular course of the condensation is not advantageous because with dropping temperatures, there is an increasingly smaller quantity of newly formed condensate, i.e. there is an increasingly smaller return flow produced for the upper region of the reflux condenser. As a consequence, the rectification becomes ineffective, and the entire reflux condensation becomes questionable

SUMMARY OF THE INVENTION

The invention is based on the object of designing a process of the type mentioned hereinabove so that the separation of $C_{2+}$ and, respectively, $C_{3+}$ or predominantly $C_4$ hydrocarbons from a gaseous mixture additionally containing lighter components is achieved in a maximally simple way in high yield and great enrichment.

This object has been attained according to the invention by providing that the gaseous mixture is initially cooled to such an extent that a portion of the $C_{2+}$, $C_{3+}$ and, respectively, $C_4$ hydrocarbons is condensed, whereupon the mixture is fed into the lower zone of a fractionating column; that a gaseous fraction is withdrawn from the upper zone of the fractionating column, this fraction being further cooled in an additional heat exchanger and partially condensed, whereupon the partially condensed proportion is introduced as return flow to the head of the fractionating column, and $C_{2+}$ or $C_{3+}$ or $C_4$ hydrocarbons are withdrawn from the bottom of the fractionating column as the product stream.

The gaseous mixture passed on to $C_4$ separation is to be of such a composition that the $C_4$ hydrocarbons represent more than 50 mol-% of the hydrocarbons contained in the gaseous mixture.

In the process of this invention, a kind of replacement circuit for a reflux condenser has been discovered surprisingly, by a relatively simple condensation procedure, retaining the substantial advantages of the reflux condenser but realizable at much lower expense In the process according to the invention, a reflux condenser is, so to speak, subdivided into three zones wherein, in a first zone (precooling), only heat exchange occurs, in a second zone (fractionating column) substantially only mass transfer takes place, and in a third zone (reflux condensation) again only heat exchange is performed.

The gaseous mixture is cooled, in the process of this invention, initially to below its dew point to such a degree that a portion of the $C_{2+}$ and/or $C_{3+}$ or $C_4$ hydrocarbons precipitates as a condensate. This cooling step, however, is conducted only to such extent that the amount of condensate obtained is relatively low and lies below 40% of the amount to be separated in total, especially below 30% and preferably below 20% of the amount of hydrocarbon to be cooled. If the amount of condensate is within higher ranges, then the amount of light components dissolved therein normally will be so large that the desired product purity for the $C_{2+}$ or $C_{3+}$ or $C_4$ fraction is not achieved since the condensate is not at all fractionated in the fractionating column, or is fractionated at least only to a small extent, because feeding takes place as low as into the bottom zone of the column.

In many cases it is practical for a favorable cooling action to provide that the dew point of the gaseous mixture is passed in the downward direction by at most 20° C., preferably by at most 10° C., if $C_4$ hydrocarbons are to be separated. Furthermore, it is very suitable to have the temperature drop below the dew point of the gaseous mixture by at most 80° C., preferably by at most 60° C., if the separation of $C_{3+}$ hydrocarbons is desired, and by at most 120° C., preferably by at most 100° C. of cooling below the dew point in case $C_{2+}$ hydrocarbons are to be separated. In this connection, it is assumed that the content of higher hydrocarbons is relatively minor as compared with the content of $C_3$ or $C_2$ hydrocarbons. In case of high proportions of heavier hydrocarbons, which, after all, lead to a high gas dew point, it is possible, in contrast to the above, to have values that drop to even lower levels below the dew point; in this connection, the subcooling step should in all instances be performed until a desired proportion of the $C_3$ or $C_2$ hydrocarbons to be separated has been condensed.

The subsequent rectification is distinguished in the process according to this invention by relatively small temperature differences between the head and bottom of the rectifying column. This temperature difference usually lies below 25° C., preferably below 20° C., for example at 15° C. In order to perform the process, a simple fractionating column is suitable having at least two equilibrium stages, e.g., a column with two to ten plates, preferably with three to six plates or, respectively, with a packing corresponding to such a number of plates.

The gaseous fraction withdrawn from the head of the fractionating column still contains a portion of $C_{2+}$ or $C_{3+}$ or $C_4$ hydrocarbons which must be recovered to obtain a desired high yield. For this purpose, the gaseous fraction is further cooled and partially condensed in a heat exchanger by indirect heat exchange. Cooling is performed to such an extent that during this step all of the constituents of heavy hydrocarbons still to be recovered are obtained in the condensate which latter is then introduced as return flow to the head of the fractionating column. The additional amount of cooling obtained by the continued cooling operation depends on the yield of heavy hydrocarbons desired, as well as on the gas composition prevailing in the individual case. Typical values for a further lowering of the temperature are at least 30° C., preferably more than 40° C., for example 50° C.

In the process according to this invention, the return flow for the rectification is already fully available at the uppermost plate of the rectifying column. Thus, heat transfer and mass transfer for the separating process are decoupled, as corresponds to the specific condensation curve of the gaseous mixture to be fractionated.

The condensate separated during the further partial condensation and recycled into the fractionating column is reheated, according to an advantageous further development of the invention, before it is fed into the fractionating column, in order to improve in this way the cold recovery of the process.

The essential idea on which this invention is based resides in that the yield of heavy hydrocarbons ($C_{2+}$, $C_{3-}$ and, respectively, $C_4$) to be separated can be set by choosing the temperature during the further cooling step, and the content of light hydrocarbons ($C_1$ and, respectively, $C_{2-}$ or $C_{3-}$ hydrocarbons) can be set by selecting the temperature to be adjusted during the precooling step, independently of each other. This makes it possible to perform the separating process, in spite of its simple operation, with a high yield as well as with a relatively high product purity. The concentration of components boiling more readily than $C_2$, $C_3$ and, respectively, $C_4$ hydrocarbons in the condensate withdrawn from the lower region of the fractionating column can be set to be below 20%, preferably below 10%, especially below 5%. On the other hand, further cooling of the gaseous fraction removed from the upper zone of the fractionating column can be effected to such an extent that the content of $C_{2+}$ and, respectively, $C_{3+}$ or $C_4$ hydrocarbons in the fraction not condensed during this step lies below 15%, preferably below 10%, especially below 5%. When performing the process of this invention, yields of $C_{2+}$, $C_{3+}$ and, respectively, $C_4$ can be obtained of 80%, preferably above especially above 95% with high product purity.

In a further embodiment of the process according to this invention, the fraction not yet condensed during further cooling can be passed on to another, third cooling stage and therein can be again subjected to partial condensation. This way of operating the process is suitable, for example, in case the gas to be fractionated has a considerable proportion of hydrogen, and the hydrogen is to be obtained in enriched form as a further product fraction. Further cooling can then be performed to such a degree that all remaining components are condensed to such an extent that a desired hydrogen purity is obtained.

Also, in an advantageous embodiment of this invention, the proportion not condensed during the further cooling of the gaseous mixture can be heated in heat exchange against the gaseous fraction to be cooled and then in heat exchange against the gaseous mixture to be cooled. After such steps, the proportion is then available at approximately ambient temperature as a further product component.

It is advantageous for covering the demand for cold of the process to engine-expand the fraction that has remained in the gaseous form after the final cooling stage, and then heat same against the process streams to be cooled off. Insofar as the thus-obtained cooling effect is not enough for covering the refrigeration requirement of the process, additional cooling can be made available by external refrigeration, for example by a cooling cycle. It is, of course, likewise possible to cover the entire cold demand by external cold if, in an individual case, the uncondensed fraction is to be passed on to further processing at low temperature.

BRIEF DESCRIPTION OF THE DRAWINGS

Additional details of the invention will be described below with reference to the embodiments illustrated schematically in the figures wherein.

DETAILED DESCRIPTION

Figure 1:
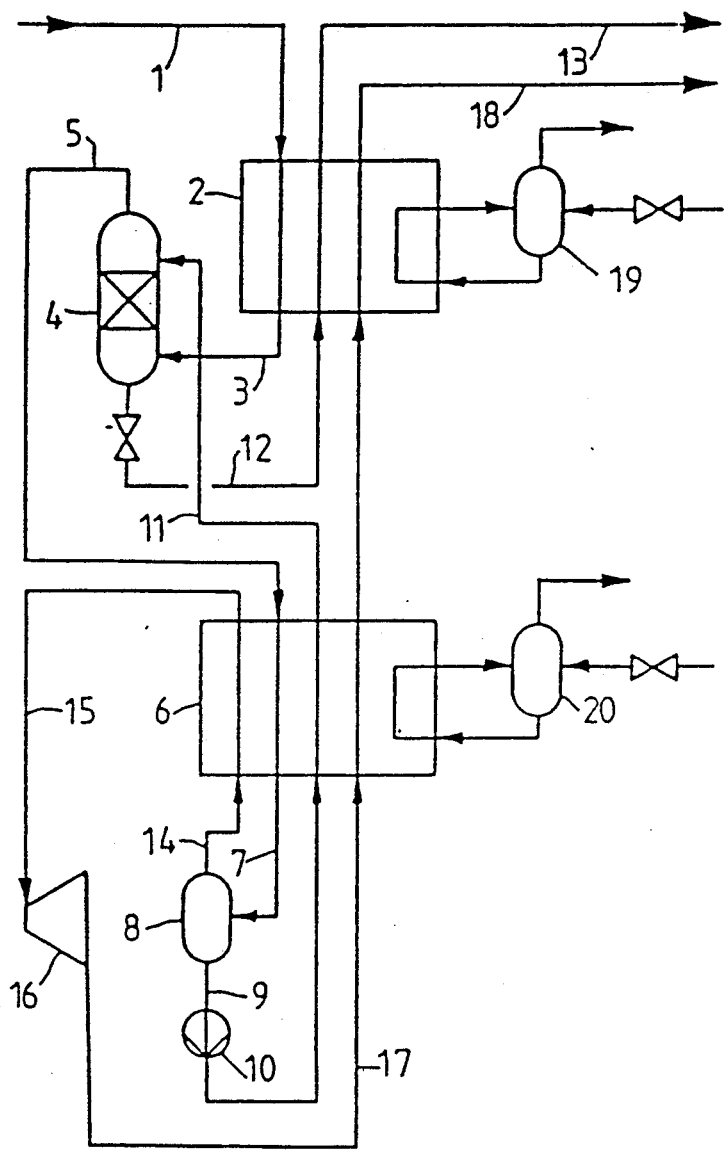
FIG. 1 shows a first embodiment of the invention.

In the embodiment illustrated in FIG. 1, the gaseous mixture to be separated is introduced via conduit 1 initially to a precooling heat exchanger 2 and cooled therein to such an extent that a portion of the heavy hydrocarbons to be separated is partially condensed. The mixture is then passed on via conduit 3 into the lower region of a fractionating column 4. The uncondensed proportions of the gaseous mixture flow through a packing arranged in the fractionating column 4, participating in a mass transfer countercurrently to downwardly flowing return-flow liquid so that additional heavy components are separated from the gaseous mixture. The gaseous fraction withdrawn from the head of the fractionating column 4 is conducted via conduit 5 to a further heat exchanger 6 and cooled therein to such a degree that the heavy hydrocarbons that have still remained in the gaseous fraction are condensed to such an extent as corresponds to the desired yield. The partially condensed stream passes via conduit 7 into a separator 8 wherein the thus-formed condensate is separated, discharged via conduit 9, and conveyed by means of the pump 10 through the heat exchanger 6 before it is finally introduced via conduit 11 to the head of the fractionating column 4 as return-flow liquid. The light constituents contained in the condensate are again separated while flowing through the fractionating column 4 and are discharged from the column via conduit 5, whereas the heavy components contained therein pass into the bottom zone and are removed therefrom, together with the constituents condensed during the precooling 2, as the bottoms product stream via conduit 12. The product stream, after heating in heat exchanger 2, is finally removed from the system by way of conduit 13.

The proportions that have remained in the gaseous phase in separator 8 are withdrawn via conduit 14, heated in heat exchanger 6, then passed on via conduit 15 to an expansion turbine 16 and therein expanded, supplying refrigeration. The expanded gas passes via conduit 17 first into heat exchanger 6 and, after flowing through the latter, finally yields its residual cold in heat exchanger 2 before being removed from the system via conduit 18 as residual gas. Insofar as the refrigeration contained in the process streams to be heated is not sufficient for cooling the gaseous mixture to be fractionated, additional refrigeration cycles 19 and, respectively, 20 can be provided.

Figure 2:
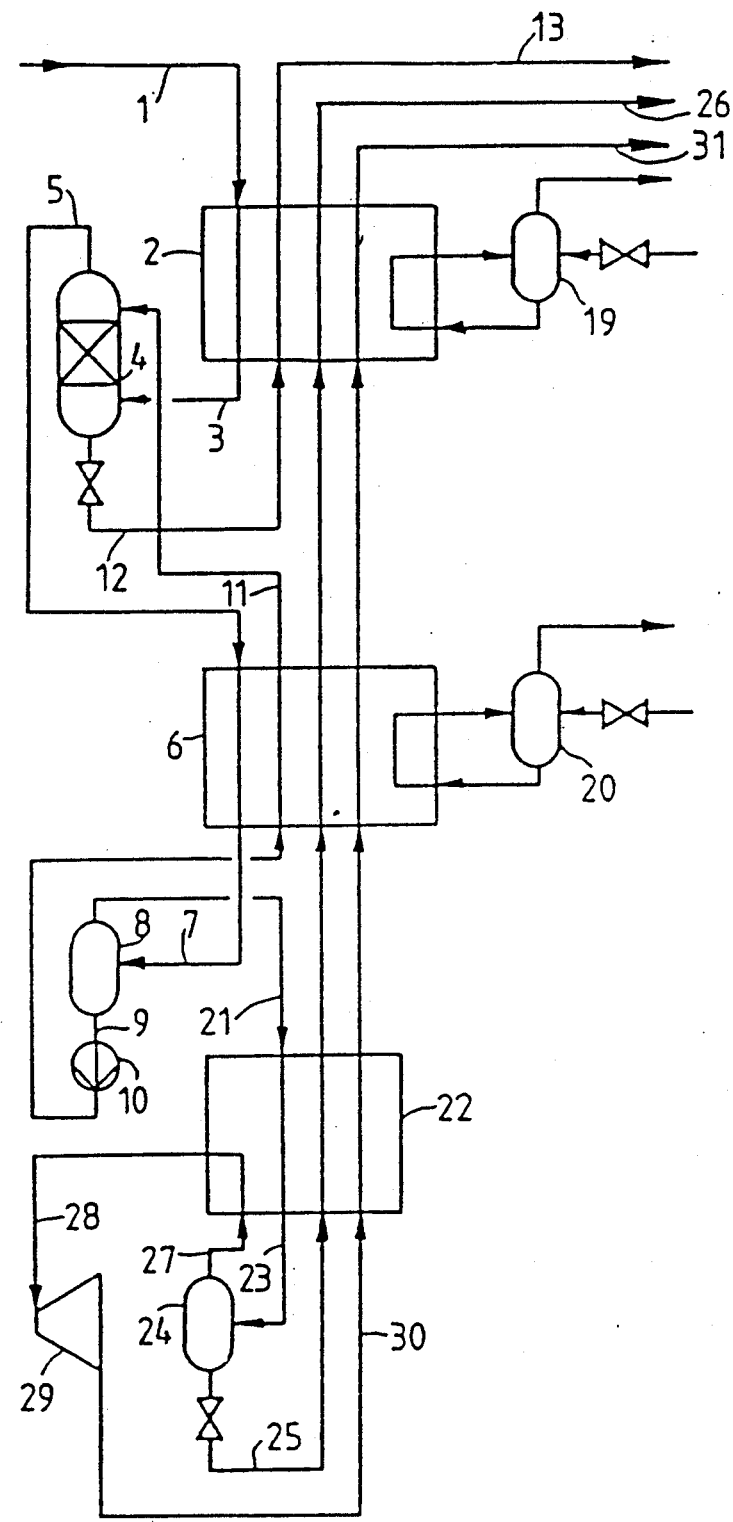
FIG. 2 shows another embodiment of the invention with a subsequently connected third cooling stage.

In the embodiment illustrated in FIG. 2 according to this invention, the gaseous fraction withdrawn from the head of separator 8 and not condensed during the further partial condensation is subjected to still another condensation step. For this purpose, the gaseous fraction is withdrawn via conduit 21 and cooled in a further heat exchanger 22 to such a degree that the remaining gaseous fraction essentially contains merely one desired component or, respectively, several desired components which can then be separately withdrawn as a further product fraction. The partially condensed gas passes via conduit 23 into a further separator 24; from the lower zone of the latter, via conduit 25, the condensate is removed and, after heating in heat exchangers 22, 6, and 2, is discharged as residual gas via conduit 26. The gaseous fraction obtained in separator 24 is fed via conduit 27 to the heat exchanger 22, partially reheated therein, then fed via conduit 28 into an expansion turbine 29, and engine-expanded. The thus-obtained refrigeration is recovered by heat exchange against process streams to be cooled; for this purpose, the gaseous mixture is conducted via conduit 30 to the heat exchangers 22, 6, and 2 before being finally withdrawn as a product stream by way of conduit 31.

Figure 3:
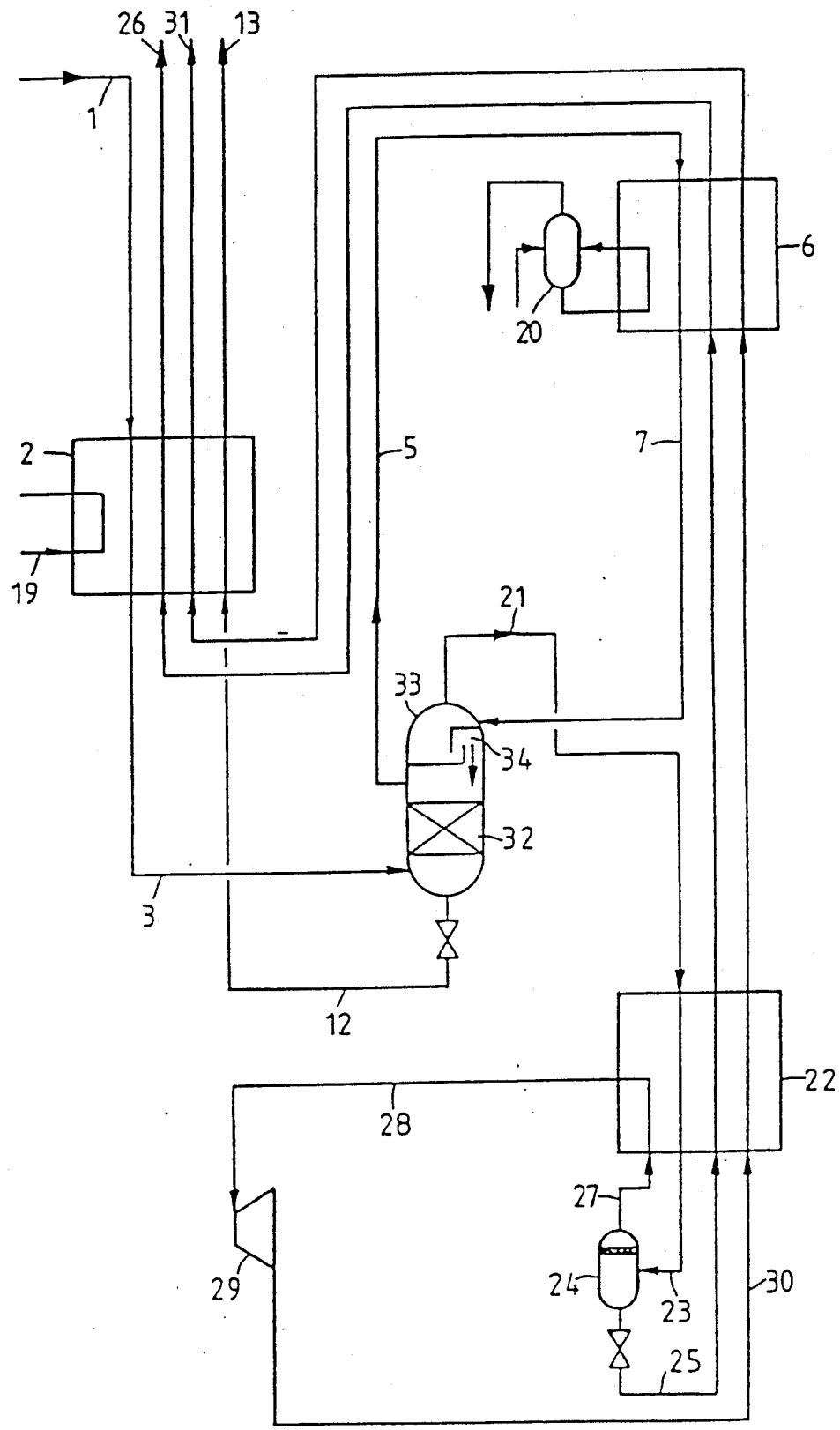
FIG. 3 shows a modification of the embodiment of the invention shown in FIG. 2.

The embodiment illustrated in FIG. 3 differs from that of FIG. 2 essentially in that the fractionating column 4 and the separator 8 are combined into one structural unit, and heat exchange of the condensate obtained in separator 8 according to FIG. 2 with the gaseous fraction to be cooled from conduit 5 is eliminated. Thereby, although the cold recovery of the process is somewhat lower, the expense for construction is, in turn, reduced since the individual separator 8, the conveying pump 10, as well as a flow cross section in heat exchanger 6, which latter will usually be a plate-type heat exchanger, are omitted. In the process of FIG. 3, the gaseous mixture enters, after being cooled in heat exchanger 2, via conduit 3 into the lower region of a fractionating column 32 operated in the same way as the fractionating column 4 according to FIGS. 1 and 2. However, the separator 8 according to FIGS. 1 and 2 is integrated into the fractionating column 32 at the head thereof. The head fraction, withdrawn via a side tap, passes via conduit 5 again to the heat exchanger 6, is partially condensed therein, and is conducted via conduit 7 into the separator 33 arranged at the head of the fractionating column. The condensate formed in heat exchanger 6 is accumulated in separator 33 at an overflow weir and from there passes, as indicated by arrow 34, directly to the head of the fractionating column 32. The fraction that has remained in the gaseous phase during partial condensation in heat exchanger 6 is discharged via conduit 21 from the fractionating column 32 and is further processed in exactly the same way as has been described in conjunction with FIG. 2.

In a concrete practical example of the invention, in a mode of operating the process in accordance with FIG. 3, a gaseous mixture containing 80.8 mol-% hydrogen, 7.1 mol-% methane, 5.6 mol-% ethane, 4.0 mol-% propane, 1.6 mol-% butane and 0.9 mol-% $C_{5+}$ hydrocarbons is supplied via conduit 1 at a temperature of 316 K and under a pressure of 38 bar. In heat exchanger 2, the gaseous mixture is cooled to 256 K, about 3.3% of the gaseous mixture being partially condensed during this step. From the head of fractionating column 32, via conduit 5, a gaseous fraction is withdrawn at a temperature of 248 K containing 84.7 mol-% hydrogen, 7.3 mol-% methane, 5.3 mol-% ethane, 2.6 mol-% propane and 0.1 mol-% butane. This fraction is cooled in heat exchanger 6 to 232 K, thus condensing about 2.8% of the fraction, and the latter is then conducted via conduit 7 into the separator 33 at the head of the fractionating column 32. The liquid introduced to the head of the column contains 2.2 mol-% hydrogen, 2.5 mol-% methane, 22.0 mol-% ethane, 61.4 mol-% propane, 11.8 mol-% butane, and 0.1 mol-% $C_{5+}$ hydrocarbons. Via conduit 12, a product stream having a temperature of 255 K is discharged from the bottom of the fractionating column 32 containing 2.1 mol-% hydrogen, 1.8 mol-% methane, 12.5 mol-% ethane, 32.8 mol-% propane, 32.7 mol-% butane and 18.1 mol-% $C_{5+}$ hydrocarbons. By way of conduit 21, a gaseous fraction is removed from separator 33 containing 84.7 mol-% hydrogen, 7.33 mol-% methane, 5.3 mol-% ethane, 2.6 mol-% propane and 0.1 mol-% butane. After further cooling in heat exchanger 22, a hydrogen-rich gaseous fraction remains which is expanded in the expansion turbine 29 to 20.5 bar and contains, besides 96.2 mol-% hydrogen, only 3.8 mol-% ethane. The condensate separated in separator 24 contains 10.6 mol-% hydrogen, 30.2 mol-% methane, 39.4 mol-% ethane, 19.1 mol-% propane and 0.7 mol-% butane. This fraction is withdrawn, after being heated up, via conduit 26 as residual gas.

In this example, a $C_3$ fraction as well as a raw hydrogen fraction are separated, without great expense, from a residual gas heretofore utilized merely as heating gas; the yield of $C_{3+}$ hydrocarbons is 61% and the hydrogen yield is 98.3%. The relatively low yield of $C_{3+}$, adequate for this concrete case, is due to the relatively minor amount of cooling of the gaseous fraction from conduit 5 in heat exchanger 6. This fact, in the concrete example, had the result that, via conduit 21, still about 60% of the propane present in the gaseous mixture was withdrawn in the gaseous phase. With a more vigorous cooling in heat exchanger 6, the yield of $C_{3+}$ of the process can be still considerably increased, for example to values between 80% and 95%.

Figure 4:
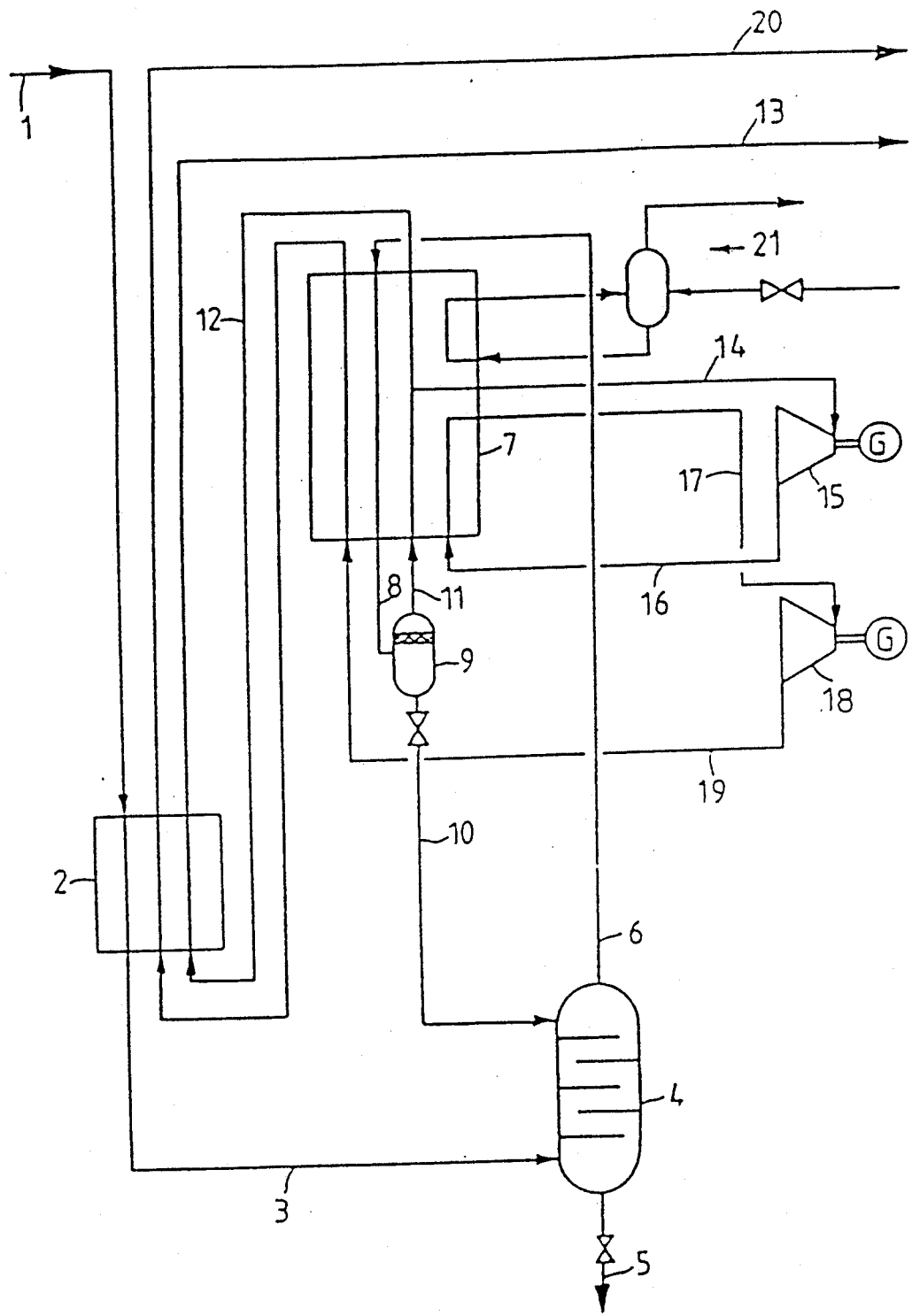
FIG. 4 shows an embodiment of the invention wherein $C_4$ hydrocarbons are separated.

In the process illustrated in FIG. 4, a feed stream coming from an isobutane dehydrogenation, containing 70.5 mol-% hydrogen, 3.5 mol-% methane, 0.5 mol-% $C_2$ hydrocarbons, 2.5 mol-% $C_3$ hydrocarbons, 9.7 mol-% $C_4$ hydrocarbons and 0.8 mol-% carbon dioxide, 0.7 mol-% carbon monoxide and 11.8 mol-% nitrogen, is introduced via conduit 1 and cooled in a heat exchanger 2 from a temperature of 290 K to 283 K. The gaseous mixture fed via conduit 1 has a pressure of 29.6 bar and is at the dew point. By precooling in heat exchanger 2, about 2.3% of the gaseous stream is condensed. The gaseous stream is fed via conduit 3 into the lower region of a rectifying column 4 wherein the $C_4$ hydrocarbons are separated from the remaining components. The $C_4$ hydrocarbons to be separated are collected in the bottom of the rectifying column and are withdrawn as product stream via conduit 5.

This product contains, besides 85.4 mol-% $C_4$ hydrocarbons, still 1.8 mol-% hydrogen, 0.6 mol-% methane, 0.4 mol-% $C_2$ hydrocarbons, 10.4 mol-% $C_3$ hydrocarbons, 0.4 mol-% carbon dioxide and 0.6 mol-% nitrogen. The product stream discharged via conduit 5 at a temperature of 282.5 K contains 99% of the $C_4$ hydrocarbons that were present in the feed gas mixture.

Via conduit 6, a gaseous fraction is withdrawn at the head of the rectifying column 4 at a temperature of 265 K, containing 79.1 mol-% hydrogen, 3.9 mol-% methane, 0.5 mol-% $C_2$ hydrocarbons, 1.5 mol-% $C_3$ hydrocarbons, 0.1 mol-% $C_4$ hydrocarbons, 0.9 mol-% carbon dioxide, 0.8 mol-% carbon monoxide and 13.2 mol-% nitrogen. This gas is cooled in a heat exchanger 7 to a temperature of 211 K, thus condensing about 10.2% of the gaseous mixture. After introducing the mixture via conduit 7 into a separator 9, phase separation is performed in the latter. The condensed proportion is returned via conduit 10 as return flow to the head of the rectifying column 4 while the uncondensed proportion is withdrawn via conduit 11 from the upper region of the separator 9. This gas contains 71.2 mol-% hydrogen, 3.6 mol-% methane, 0.7 mol-% $C_2$ hydrocarbons, 8.4 mol-% $C_3$ hydrocarbons, 2.4 mol-% $C_4$ hydrocarbons, 1.0 mol-% carbon dioxide, 0.7 mol-% carbon monoxide and 11.9 mol-% nitrogen. This gas is heated in heat exchanger 7 against the gaseous fraction to be cooled from the rectifying column 4 and thereafter passes by way of conduit 12 to heat exchanger 2 wherein it is further heated against the gaseous mixture to be cooled before it is finally discharged via conduit 13 as residual gas fraction at a temperature of 287 K and under a pressure of 28.5 bar. In order to cover the refrigeration requirement of the process, a partial stream of the residual gas stream which is partially heated in heat exchanger 7 and withdrawn via conduit 11 is branched off via conduit 14 and engine-expanded. For this purpose, the gas is first expanded to an intermediate pressure in an expansion turbine 15, then again passed through heat exchanger 7 via conduit 16, and, after being partially heated in this heat exchanger, fed via conduit 17 to a second expansion turbine 18 wherein it is further expanded to a lower pressure and thereafter discharged via conduit 19. The cold gas in conduit 19 is initially heated in heat exchanger 7 and then in heat exchanger 2 against process streams to be cooled before it is finally discharged as low-pressure residual gas by way of conduit 20.

In order to cover further demand for cold in heat exchanger 7, a refrigeration cycle indicated by 21 can be provided.

I claim:

1. A process for separating $C_{2+}$ or $C_{3+}$ or $C_4$ hydrocarbons from a gaseous mixture containing these components and lower-boiling constituents, predominantly hydrogen, said process comprising:

initially cooling and partially condensing said gaseous mixture so that only a minor portion of the $C_{2+}$, $C_{3+}$ or, respectively, $C_4$ hydrocarbons is condensed;

delivering the partially condensed mixture into a lower zone of a fractionating column;

withdrawing a gaseous fraction from an upper zone of said fractionating column;

further cooling and partially condensing said gaseous fraction in an additional heat exchanger whereupon the resultant condensed proportion is introduced as return flow to said upper zone of said fractionating column and the resultant uncondensed portion is subjected to engine expansion and thereafter heated by heat exchange with process streams to be cooled; and recovering $C_{2+}$, $C_{3+}$ or, respectively, $C_4$ hydrocarbons from said lower zone of said fractionating column as a product stream.

2. A process according to claim 1, wherein said partially condensed proportion of said gaseous fraction is heated before being introduced into said fractionating column.

3. A process according to claim 1, wherein said fractionating column is operated with a temperature difference of less than 25° C., between said upper and lower zones.

4. A process according to claim 1, where said further cooling of said gaseous fraction from said upper zone of said fractionating column lowers the temperature thereof by at least 30° C.

5. A process according to claim 1, wherein said gaseous mixture is cooled initially only to such a degree that, in the thus-formed condensate, the concentration of the components boiling lower than $C_2$, $C_3$ or, respectively, $C_4$ hydrocarbons is below the concentrations of $C_{2+}$, $C_{3+}$ or, respectively, $C_4$ in said product stream.

6. A process according to claim 5, wherein said concentration of the components boiling lower than $C_2$, $C_3$ or $C_4$ hydrocarbons in said thus-formed condensate is below 20 mol %.

7. A process according to claim 1, wherein said further cooling of said gaseous fraction withdrawn from said upper zone of said fractionating column is effected to such an extend that the content of $C_{2+}$, $C_{3+}$ or, respectively, $C_4$ hydrocarbons in the resultant uncondensed portion of said gaseous fraction is below 15 mol %.

8. A process according to claim 1, wherein, prior to said engine expansion and heat exchange with process streams to be cooled, said uncondensed portion resulting from said further cooling of said gaseous fraction is introduced into a third cooling stage and is subjected to a further partial condensation.

9. A process according to claim 1, wherein the uncondensed portion resulting from said further cooling of said gaseous fraction from said upper zone of said fractionating column is heated in heat exchange with said gaseous fraction and thereafter heated in heat exchange with said gaseous mixture.

10. A process according to claim 1, wherein the hydrocarbons contained in said gaseous mixture consists of 50-70 mol% $C_4$ hydrocarbons, 15-40 mol% methane and 0-25 mol% $C_2$ and $C_3$ hydrocarbons.

11. A process according to claim 3, wherein said temperature difference is less than 20° C.

12. A process according to claim 4, wherein said temperature is lowered by more than 40° C.

13. A process according to claim 6, wherein said concentration is below 10 mol%.

14. A process according to claim 6, wherein said concentration is below 5 mol%.

15. A process according to claim 7, wherein said content is below 10 mol%.

16. A process according to claim 7, wherein said content is below 5 mol%.

17. A process according to claim 1, wherein a part of the condensed portion resulting from said further cooling of said gaseous fraction is branched off, engine expanded, heated against process streams to be cooled, engine expanded again, and again heated against process streams to be cooled.

18. A process according to claim 1, wherein said minor portion is below 30 mol% of the amount of $C_{2+}$, $C_{3+}$ or, respectively, $C_4$ hydrocarbons to be separated.

19. A process according to claim 1, wherein said minor portion is below 20 mol% of the amount of $C_{2+}$, $C_{3+}$ or, respectively, $C_4$ hydrocarbons to be separated.

20. A process according to claim 1, wherein said process is for the separation of $C_4$ hydrocarbons and the initial cooling and partial condensation of said gaseous mixture reduces the temperature thereof by at most 20° C.

21. A process according to claim 1, wherein said process for the separation for $C_{3+}$ hydrocarbons and said initial cooling and partial condensation of said gaseous mixture reduces the temperature thereof by at most 80° C.

22. A process according to claim 5, wherein said process is for the separation of $C_{2+}$ hydrocarbons and said initial cooling and partial condensation of said gaseous mixture thereof reduces the temperature of said gaseous mixture by at most 120° C.

23. A process according to claim 1, wherein said fractionating column contains 2-10 theoretical or actual plates.

24. A process according to claim 1, wherein said product stream is recovered from said lower zone of said fractionating column without further purification or heat exchange with said gaseous fraction.

25. A process according to claim 1, wherein said process provides a yield of $C_{2+}$, $C_{3+}$ or, respectively, $C_4$ hydrocarbons in said product stream of at least 80 mol%.

* * * * *